United States Patent [19]

Kurtzberg et al.

[11] Patent Number: 5,567,625
[45] Date of Patent: Oct. 22, 1996

[54] APPARATUS AND METHOD FOR REAL-TIME SPECTRAL DECONVOLUTION OF CHEMICAL MIXTURES

[75] Inventors: Jerome M. Kurtzberg, Yorktown Heights; John S. Lew, Ossining, both of N.Y.

[73] Assignee: International Business Machines Corporation, Armonk, N.Y.

[21] Appl. No.: 326,101

[22] Filed: Oct. 19, 1994

[51] Int. Cl.⁶ .................................................. G01N 21/25
[52] U.S. Cl. .................... 436/164; 422/68.1; 422/82.05; 422/77; 436/805
[58] Field of Search .................................... 436/164, 805; 422/68.1, 77, 82.05, 82.11

[56] References Cited

U.S. PATENT DOCUMENTS

| | | |
|---|---|---|
| 2,866,899 | 12/1958 | Busignies et al. . |
| 4,807,148 | 2/1989 | Lacey . |
| 4,847,792 | 7/1989 | Barna et al. . |
| 4,885,254 | 12/1989 | Sung . |
| 4,986,658 | 1/1991 | Kim . |
| 5,014,217 | 5/1991 | Savage . |
| 5,023,804 | 6/1991 | Hoult . |
| 5,046,846 | 9/1991 | Ray et al. . |
| 5,121,337 | 6/1992 | Brown . |
| 5,121,338 | 6/1992 | Lodder . |
| 5,124,932 | 6/1992 | Lodder . |
| 5,218,299 | 6/1993 | Dunkel . |
| 5,242,602 | 9/1993 | Richardson et al. . |

*Primary Examiner*—Lyle A. Alexander
*Attorney, Agent, or Firm*—Daniel P. Morris

[57] ABSTRACT

An apparatus and method are described for determining the relative concentrations of the constituent chemical components of a chemical combination. The spectral response of the composite sample, measured at a number of wavelengths $\lambda_i$, is represented by a vector C. The relative concentration of the jth constituent is $X_j$, and the relative concentrations of each of the chemical constituents are represented by the vector X. The vector X can be determined from the vector C by the following matrix equation:

$$X = (A^T A)^{-1} A^T C$$

wherein the matrix A has elements $A_{ij}$, which is the spectral response of the jth component at wavelength $\lambda_i$. Since the matrix A is a predetermined set of numbers, the elements of vector X are readily determined from the above equation. Such a determination is rapid; a profile of each of the constituents $X_j$ in the sample is readily and rapidly determined.

28 Claims, 3 Drawing Sheets

APPARATUS AND METHOD FOR REAL-TIME SPECTRAL DECONVOLUTION OF CHEMICAL MIXTURES

FIELD OF THE INVENTION

The present invention is directed to a method, system and apparatus for deconvolving chemical mixtures into the constituent components of the chemical mixture.

BACKGROUND OF THE INVENTION

Contemporary technology offers many instances that require rapidly identifying the constituents of a chemical mixture. The chemical mixture can be a solid, a liquid or a gas. In the semiconductor industry numerous multilayered structures are made, for example on semiconductor chips or semiconductor chip packaging substrates. In order to monitor the quality of the products being fabricated, it may be necessary to determine the profile of various chemical species in the multilayer structure. This can be done by ablating away the material from the surface and analyzing the material that is ablated away. For such a process to have practical value, it is imperative that the ablating or etching away of the material be done rapidly and that the analysis of the etched or ablated material be performed rapidly.

In the case of a chemical fabrication process for a liquid, it may be desirable to monitor continually the constituent components of the liquid formed by the process. For such monitoring to have value in practical use, it is imperative that the analysis of the liquid be done rapidly so that, as the liquid flows past the monitoring point, an analysis can be done at a closely spaced sequence of times.

As another example, in order to comply with increasingly stringent environmental standards it may be necessary to reduce pollutants emitted into the atmosphere by smokestacks of a manufacturing facility. To do this it may be necessary to monitor continually the chemical constituents of the gases emitted by a smokestack. To do this efficiently it may be necessary to determine these constituents at closely spaced times.

As another example, it may be desirable to construct apparatus that can be controlled so that it runs at peak efficiency, an illustrative example being a gasoline engine. To maximize the efficiency of such an engine, and minimize the pollutants in its exhaust emissions, it may become imperative to monitor continually the chemical constituents in the exhaust from the engine, and the chemical constituents of the fuel entering the engine, so that a feedback control mechanism from the exhaust monitoring can achieve the stated goals. Such an engine would require continually monitoring, at closely spaced intervals of time, the chemical constituents of the exhaust and of the fuel input.

U.S. Pat. No. 2,866,899 to Busignies et al. describes an electronic spectroanalysis computer. The apparatus quantitatively analyzes an infrared absorption spectrum of a multicomponent sample to provide a quantitative deconvolution, i.e., a decomposition of the complex spectrum in terms of the constituents' spectra. The technique involves integrations as shown in equations 10 and 11 of Busignies et al.; these integrations are time-consuming and therefore inefficient.

It is an object of the present invention to provide a system, method, and apparatus for providing the relative concentration of chemical constituents of a composite sample, and for doing this with minimum computation time.

SUMMARY OF THE INVENTION

A broad aspect of the present invention is an apparatus for determining the relative concentrations $X_j$ of N component chemical constituents, wherein $j=1$ to N, in a chemical combination using predetermined relative constituents' spectral-analysis intensities $A_{ij}$ of said N component chemical constituents, wherein $i=1$ to M and wherein $M \geq N$. The apparatus contains a means for providing relative spectral intensities $C_i$ of the chemical combination at wavelengths $\lambda_i$; a means for determining the relative concentrations $X_j$ from equation $$X = (A^T A)^{-1} A^T C$$

wherein A is a matrix of the relative spectral intensities $A_{ij}$, $A^T$ is the transpose of matrix A, and $(A^T A)^{-1}$ is the inverse matrix of $A^T A$. Also, X is a column vector of the relative concentrations $X_j$, and C is a column vector of the relative spectral intensities $C_i$. The result is adjusted to eliminate negative values.

Another broad aspect of the present invention is a method for determining the relative concentrations $X_j$ of N component chemical constituents, wherein $j=1$ to N, in a chemical combination using predetermined relative constituents' spectral intensities $A_{ij}$ of said N component chemical constituents, wherein $i=1$ to M and wherein $M \geq N$. The method includes the steps of providing relative spectral intensities $C_i$ of the chemical combination at wavelengths $\lambda_i$, and determining the relative concentrations $X_j$ from equation $$X = (A^T A)^{-1} A^T C$$

The result is adjusted to eliminate negative values to ensure nonnegativity.

In a more particular aspect of the apparatus and method of the present invention, the relative spectral intensities $A_{ij}$ and $C_i$ are absorbance intensities which are generated by an absorbance spectrometer.

BRIEF DESCRIPTION OF THE DRAWINGS

These and other objects, features and advantages of the present invention will become apparent upon consideration of the following detailed description of the invention when read in conjunction with the drawings and figures, in which.

DETAILED DESCRIPTION

For the purpose of easily understanding the details of the present invention, it will be described in terms of analyzing the chemical constituents of a semiconductor wafer. This is exemplary only and not limiting. The process of forming a semiconductor wafer on which integrated circuits are formed is well known. In such processing, the wafers are exposed to a sequence of chemical steps, heat treatments and mechanical operations. During this processing, it is generally known, from knowledge of the chemistry, what types of chemical compounds are included in the semiconductor wafer as each layer of an integrated circuit is formed. This knowledge can come from information about the chemicals which are being deposited as well as from understanding of the chemical reactions occurring at a surface, reactions which may form other chemical compounds. Thus, from this knowledge of the base processing of the semiconductor wafer, it is known that, in this wafer, there is a set of N possible chemical component constituents. In order to diagnose problems associated with the fabrication process for a semiconductor wafer, it is desirable to monitor the fabrication process so as to analyze the wafer, i.e., to determine the actual profile of each of the N chemical component constituents from the surface of the fully fabricated semiconductor device down to a depth into the substrate.

The apparatus described herein constitutes an apparatus in which such a semiconductor wafer can be placed, and in which there is a means to remove material, in sequence of time, from the surface of the substrate. The removed material is exposed with radiation and the absorption spectrum is measured. The apparatus, according to the present invention, provides a means for determining the relative concentrations of each of the N component chemical constituents contained in the sample being measured.

Figure 1:
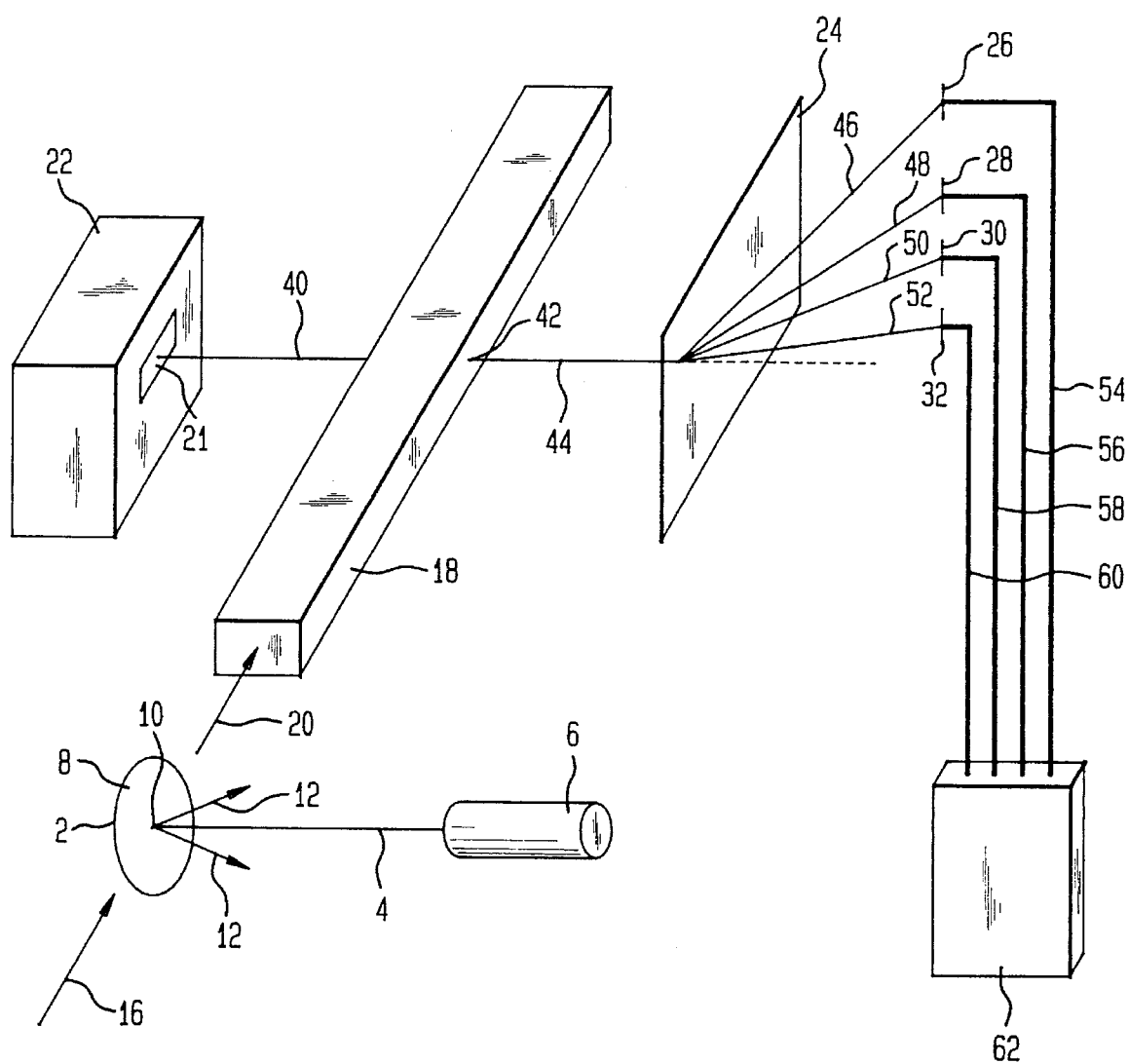
FIG. 1 is a schematic diagram of an embodiment of the apparatus according to the present invention.

FIG. 1 is a schematic diagram of an apparatus, according to the present invention, for determining profiles of chemical constituents of a semiconductor wafer 2. Wafer 2 is contained within a chamber not shown. Wafer 2 is subjected to an ion beam 4 generated by ion beam source 6. The ion beam can be any ion beam, for example, an argon ion beam. The beam 4 etches material from the surface 8 of wafer 2 at location 10, generating in the immediate vicinity of location 10 particles represented by arrows 12. An inert gas stream 16, such as an argon gas stream, carries the particles 12 into tube 18 as shown by arrow 20. Tube 20 is preferably a quartz or pyrex tube having square or rectangular cross section. Tube 18 is fed into an absorbance spectrometer, which is represented by light source 22, tube 18, grating 24 and detectors 26, 28, 30 and 32. An absorbance spectrometer useful to practice the present invention is Hewlett Packard Model 8452A Diode Array Spectrophotometer; it will be apparent to those of skill in the art how to modify such an absorbance spectrometer to practice the present invention. Light source 22 of the absorbance spectrometer has a slit through which radiation beam 40 emerges collimated and passes through tube 18 at location 42. The beam emerges as beam 44, which passes through grating 24, which splits beam 44 into beams 46, 48 50 and 52. Each of these has a different wavelength 2 of beam 44 incident on the grating 44. Beams 46, 48, 50 and 52 are incident to detectors 26, 28, 30 and 32 respectively. Four detectors are shown for example only; in a typical apparatus there are many more detectors. Detectors 26, 28, 30 and 32 are connected by lines 54, 56, 58 and 60, respectively, to computer 62.

Figure 2:
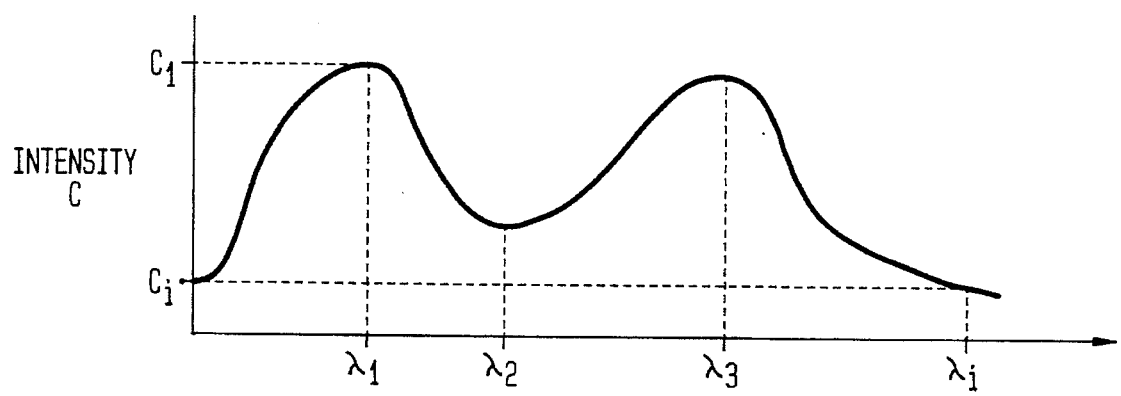
FIG. 2 is a schematic diagram of an absorption spectrum of a chemical combination.
Figure 3:
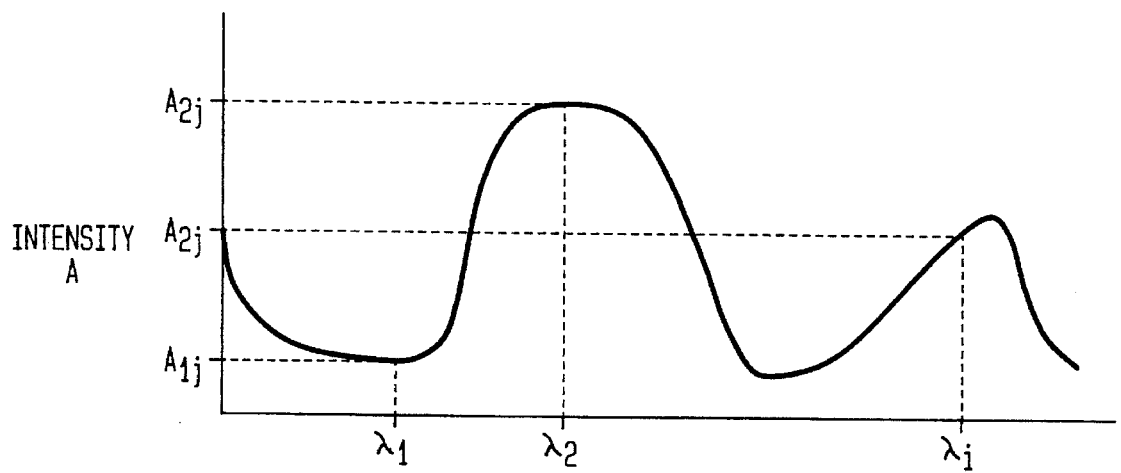
FIG. 3 is a schematic diagram of an absorption spectrum of the jth chemical constituent.

FIG. 2 is a schematic diagram of an absorption spectrum of a chemical combination, and FIG. 3 is a schematic diagram of the jth chemical constituent.

Before gas stream 20 is permitted to flow into tube 18, beam 40 is allowed to irradiate tube 18 so that computer 62 can record an intensity at each of the detectors. This is clone because for each wavelength 2 the detectors will have a different sensitivity, represented by $I_0(\lambda)$. Gas stream 20 is then permitted to flow through tube 18; next, incident beam 40 from light source 22 passes through tube 18, which contains the gas stream 20. Detectors 26, 28, 30 and 32 now measure the radiation intensity, after passing through gas stream 20, as $I(\lambda)$. If there is no absorption at a particular wavelength, thee ratio of I to $I_0$ is 1. The absorption spectrum can be represented by the plot of either this ratio or its reciprocal. (The amount absorbed is proportional to 1 minus the former ratio.) The values of the most convenient ratio $R(\lambda)$ are stored in computer 20 for all values of $\lambda$.

Since it is known what are the expected chemical constituents of the gas stream 20, the absorption spectrum of each constituent is also measured and stored in computer 20. The absorption spectrum of each constituent can be measured using the Hewlett Packard Model 8452A Diode Array Spectrophotometer by inserting into the spectrophotometer a quartz or pyrex Cuvett filled with the particular chemical constituent.

A spectrum is generated as described above for each chemical constituent. Each of the j=1 to N chemical constituents is measured and the absorbance values $A_{ij}$ at wavelengths $\lambda_2$, where i=1 to M, are stored in computer 20. The absorption spectrum of the composite sample, which is comprised of at least one of the chemical constituents, is measured, and the value of the absorbance $C_i$ at $\lambda_i$ of the composite sample is stored in computer 20. The absorbance $C_i$ is equal to a linear combination of the absorbances of all the chemical constituents, wherein each chemical constituent has a concentration $X_j$, and is represented by the following equation:

$$C_i = \sum_{j=1}^{N} A_{i,j} X_j \qquad (1)$$

Equation 1 can be represented in matrix form as equation 2:

$$C = AX \qquad (2)$$

wherein C is a column vector having elements ($C_1$, $C_2$, $C_3$, ... $C_M$), wherein X is the column vector having elements ($X_1$, $X_2$, $X_3$, ... $X_N$), and wherein matrix A is a matrix of the elements $A_{ij}$. If matrix A has an inverse $A^{-1}$, then Equation 2 has a solution:

$$X = A^{-1} C \qquad (3)$$

But A has an inverse only if the matrix A is square and if its rows (or equivalently columns) are linearly independent. However, in this case the resulting values of the concentrations $X_j$ will then have rather sensitive dependence on the values of the matrix elements $A_{ij}$, so that slight measurement errors in matrix elements $A_{ij}$ may generate appreciable errors in computed concentrations $X_j$.

To reduce such $X_j$ errors, it is desirable to incorporate measured values of both sample spectrum and component spectra at more wavelengths, that is, to make and use measurements at more wavelengths than there are constituent chemical components. Then M>N. Indeed, choosing M significantly larger than N admits a substantially greater amount of data sampling, which will yield a more precise determination of the concentrations $X_j$ of the chemical constituents.

But, in Equation 2, A is now no longer a square matrix, so that the analogous procedure now needs a substitute for Equation 3. Thus, to determine the values of the vector X, the method, system and apparatus according to the present invention utilize the following relationship:

$$X = BC \qquad (4)$$

wherein matrix B is a pseudo-inverse, which is given by the following equation:

$$B = (A^T A)^{-1} A^T \qquad (5)$$

wherein $A^T$ is the transpose of the matrix A, and wherein $(A^T A)^{-1}$ indicates the inverse of the product matrix of $A^T A$.

Details about the computation and use of the pseudo-inverse can be found in the book Regression and the Moore-Penrose Pseudo-Inverse, Academic Press, New York, 1972, author Albert.

Since the pseudo-inverse B is based only on elements of the matrix A, therefore the matrix B elements can be calculated and stored in the computer before any measurements are made of a composite sample under test. Therefore, computations to determine the components of the vector X are very rapid.

Figure 4:
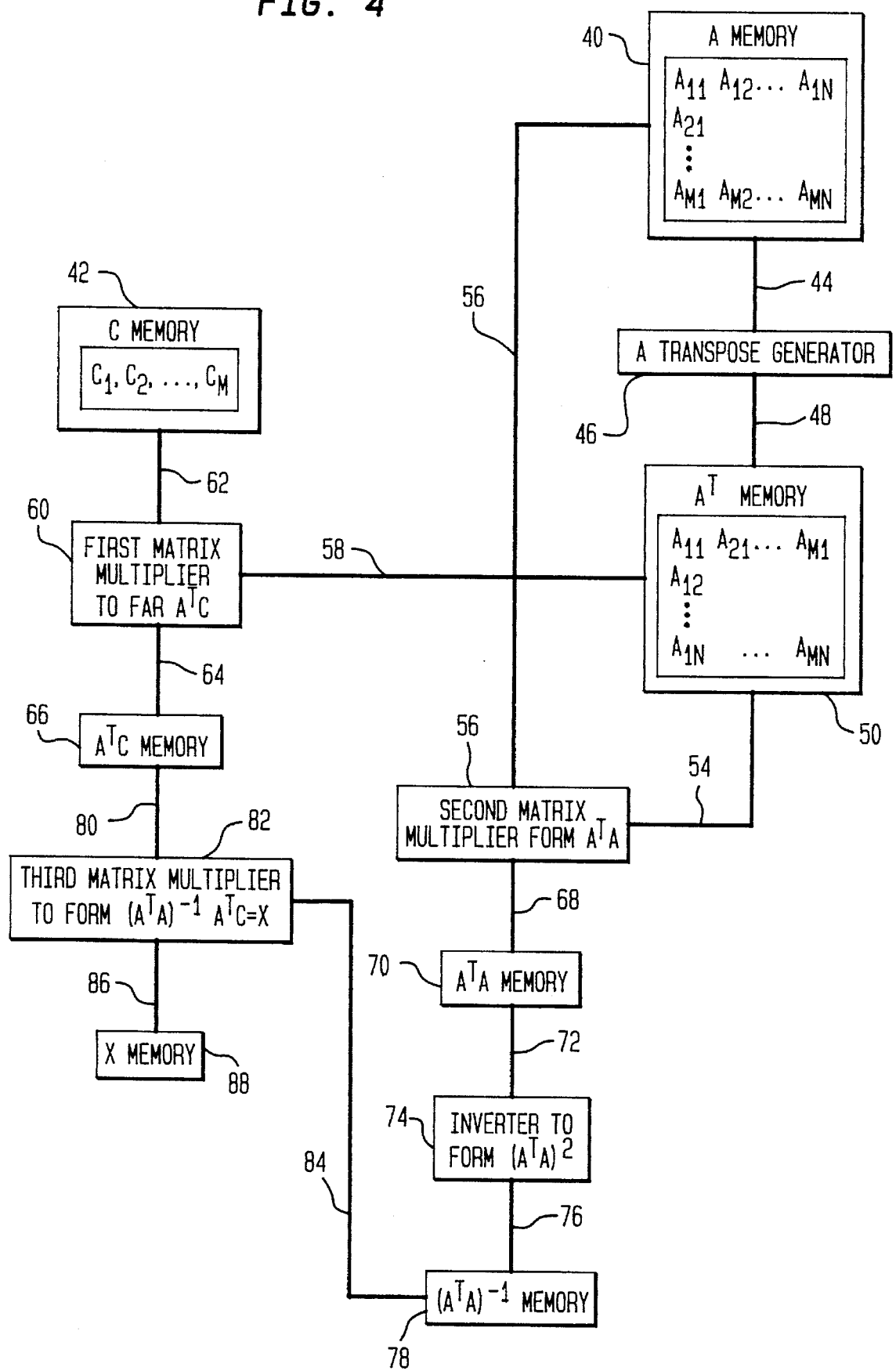
FIG. 4 is a schematic diagram of a method according to the present invention to determine X.

FIG. 4 is a schematic diagram of a method according to the present invention to determine X, the vector of concentrations. In computer 62 matrix A is stored in A-memory 40. The vector C of relative spectral intensities of the chemical combination is stored in C-memory 42. As indicated by line 44 computer control is transferred to A-transpose-generator 46. As indicated by line 48 the generated transpose $A^T$ is stored in the $A^T$-memory 50. As indicated by line 58 the elements of the $A^T$-matrix are moved from the $A^T$-memory 50 to the first multiplier 60 and as indicated by line 62 the elements of the C-vector are transferred from the C-memory 42 to the first multiplier 60. First multiplier 60 performs the operation $A^T C$ which is stored in $A^T C$-memory 66. As indicated by line 52 the elements of the A matrix are transferred from the A-memory 40 to the second multiplier 56 and as indicated by line 54 the elements of the $A^T$ matrix are transferred from the $A^T$-memory 50 to the second multiplier 56 which generates $A^T A$ which as indicated by line 68 is stored in the $A^T A$-memory 70. As indicated by line 72 the elements of the $A^T A$ memory 74 are transferred to inverter 74 which generates $(A^T A)^{-1}$ which is stored in the $(A^T A)^{-1}$-memory 78. As indicated by line 80 the elements of the $A^T C$-memory 66 are transferred to the third multiplier 82 and as indicated by line 84 the elements of the $(A^T A)^{-1}$-memory 78 are transferred to the third multiplier 82 to generate the elements of X which are transferred as indicated by line 86 to X-memory 88.

While the present invention has been shown and described with vectors as the specific embodiments, it will be understood that it is not thus limited. Numerous modifications, changes and improvements will occur which fall within the scope and spirit of the invention.

What is claimed is:

1. An apparatus for determining the concentrations $X_j$ of N component chemical constituents, wherein j=1 to N, in a chemical combination using predetermined relative constituent spectral intensities $A_{ij}$ of said N component chemical constituents, wherein i=1 to M, wherein M>N, comprising:

means for providing relative spectral intensities $C_i$ of said chemical combination at wavelengths $\lambda_i$;

means for determining said concentrations $X_j$ from equation $$X=(A^T A)^{-1} A^T C$$

wherein A is a matrix of said relative spectral intensities $A_{ij}$, wherein $A^T$ is the transpose of A, and wherein $(A^T A)^{-1}$ is the inverse matrix of $A^T A$, wherein X is a vector of said concentrations $X_j$, and C is a vector of said relative spectral intensities $C_i$.

2. An apparatus according to claim 1, wherein said relative spectral intensities $A_{ij}$ and $C_i$ are absorbance intensities.

3. An apparatus according to claim 1, wherein said means for providing said relative spectral intensities $C_i$ is an absorbance spectrometer.

4. An apparatus according to claim 1, wherein said predetermined relative spectral intensities $A_{ij}$ are determined using an absorbance spectrometer.

5. An apparatus according to claim 1, wherein said means for determining is a digital computer.

6. An apparatus according to claim 5, wherein said predetermined relative spectral intensities $A_{ij}$ are stored in said digital computer.

7. An apparatus according to claim 1, wherein if a particular $X_j$ is determined to be less than zero, said particular $X_j$ is set equal to zero.

8. An apparatus according to claim 1, further including a means for generating said relative spectral intensities $C_i$ at a plurality of periodic intervals in time.

9. An apparatus according to claim 8, wherein said interval of time is less than a millisecond.

10. An apparatus according to claim 1, wherein said chemical combination is selected from the group consisting of a solid, a liquid and a gas.

11. An apparatus according to claim 8, wherein said chemical combination is a solid, and further including a means for removing a portion of material at a surface of said solid, said chemical combination being said portion at each of said plurality of said time intervals, a vector X being generated for each of said time intervals, said time interval corresponding to a depth into said surface, further including a means for generating a profile of at least one of said relative concentrations $X_j$ versus said depth.

12. An apparatus for determining, at periodic intervals of time, the concentrations $X_j$ of N component chemical constituents, wherein j=1 to N, in a chemical combination using predetermined relative constituent spectral intensities $A_{ij}$ of said N component chemical constituents, wherein i=1 to M, wherein M>N, comprising:

means for providing relative spectral intensities $C_i$ of said chemical combination at wavelengths $\lambda_i$ at said periodic intervals of time;

means for determining said concentrations $X_j$ from equation $$X=(A^T A)^{-1} A^T C$$

wherein A is a matrix of said relative constituent spectral intensities $A_{ij}$, wherein $A^T$ is the transpose of A and wherein $(A^T A)^{-1}$ is the inverse matrix of $A^T A$, wherein X is a vector of said relative concentrations $X_j$ and C is a vector of said relative spectral intensities $C_i$;

an electromagnetic radiation source for providing an incident beam containing said $\lambda_i$, said beam having an intensity $I_0(\lambda_i)$ at each of said $\lambda_i$;

an enclosure through which said chemical combination passes, said enclosure being transparent to said $\lambda_i$;

a means for directing said incident beam at said enclosure through which said beam passes as a transported beam;

means for measuring each of said $I_0(\lambda_i)$;

means for measuring the intensity $I(\lambda_i)$ of the transported beam at each of said $\lambda_i$;

means for comparing $I_0(\lambda_i)$ and $I(\lambda_i)$ for each of said $\lambda_i$ to determine each of said $C_i$;

means for generating a profile of at least one of said relative concentrations $X_j$ versus said periodic intervals of time.

13. A method for determining the concentrations $X_j$ of N component chemical constituents, wherein j=1 to N, in a chemical combination using predetermined relative constituent spectral intensities $A_{ij}$ of said N component chemical constituents, wherein i=1 to M, wherein M>N, comprising the steps of:

providing relative spectral intensities $C_i$ of said chemical combination at wavelengths $\lambda_i$;

determining said relative concentrations $X_j$ from equation $$X = (A^T A)^{-1} A^T C$$

wherein A is a matrix of said relative spectral intensities $A_{ij}$, wherein $A^T$ is the transpose of A, and wherein $(A^T A)^{-1}$ is the inverse matrix of $A^T A$, and X is a vector of said relative concentrations $X_j$, and C is a vector of said relative spectral intensities $C_i$.

14. A method according to claim 13, wherein said relative spectral intensities $A_{ij}$ and $C_i$ are absorbance intensities.

15. A method according to claim 13, wherein said step of generating said relative spectral intensities $C_i$ is using an absorbance spectrometer.

16. A method according to claim 13, wherein said predetermined relative spectral intensities $A_{ij}$ are determined using an absorbance spectrometer.

17. A method according to claim 13, wherein said step of determining is done using a digital computer.

18. A method according to claim 16, wherein said predetermined relative spectral intensities $A_{ij}$ are stored in said digital computer.

19. A method according to claim 13, wherein if a particular $X_j$ is determined to be less than zero, said particular $X_j$ is set equal to zero.

20. A method according to claim 13, further including a step of generating said relative spectral intensities $C_i$ at a plurality of periodic intervals in time.

21. A method according to claim 19, wherein said interval of time is less than a millisecond.

22. A method according to claim 13, wherein said chemical combination is selected from the group consisting of a solid, a liquid and a gas.

23. A method according to claim 19, wherein said chemical combination is a solid, and further including a step for removing a portion of material at a surface of said solid, said chemical combination being said portion at each of said plurality of said time intervals, a vector X being generated for each of said time intervals, said time interval corresponding to a depth into said surface, further including a step of generating a profile of at least one of said relative concentrations $X_j$ versus said depth.

24. An apparatus according to claim 1, wherein said concentration $X_j$ are selected from the group consisting of relative concentrations and absolute concentrations.

25. A method according to claim 13, wherein said concentrations $X_j$ are selected from the group consisting of relative concentrations and absolute concentrations.

26. An apparatus according to claim 1, further including:

means for storing said $C_i$ as stored relative spectral intensities;

means for storing said $A_{ij}$ as stored predetermined relative constituent spectral intensities.

27. A structure according to claim 1, wherein said chemical combination is a chemical mixture.

28. A method according to claim 13, wherein said chemical combination is a chemical mixture.

* * * * *